United States Patent [19]
Gehlert et al.

[11] Patent Number: 5,281,624
[45] Date of Patent: Jan. 25, 1994

[54] N-ALKYL-3-PHENYL-3-(2-SUBSTITUTED PHENOXY) PROPYLAMINES AND PHARMACEUTICAL USE THEREOF

[75] Inventors: Donald R. Gehlert, Indianapolis; David W. Robertson, Greenwood; David T. Wong, Indianapolis, all of Ind.

[73] Assignee: Eli Lilly and Company, Indianapolis, Ind.

[21] Appl. No.: 766,993

[22] Filed: Sep. 27, 1991

[51] Int. Cl.$^5$ .................. A61K 31/135; C07C 323/37
[52] U.S. Cl. ...................................... 514/651; 564/347
[58] Field of Search .................... 564/347; 514/651

[56]  References Cited
U.S. PATENT DOCUMENTS

| | | | |
|---|---|---|---|
| 4,018,895 | 4/1977 | Molloy et al. | 424/330 |
| 4,194,009 | 3/1980 | Molloy et al. | 514/651 |
| 4,313,896 | 2/1982 | Molloy et al. | 564/347 X |
| 4,314,081 | 2/1982 | Molloy et al. | 564/347 |
| 4,584,404 | 4/1986 | Molloy et al. | 564/347 |
| 4,626,549 | 12/1986 | Molloy et al. | 514/651 |

FOREIGN PATENT DOCUMENTS 336753 10/1989 European Pat. Off. .

OTHER PUBLICATIONS

Wong et al., "An New Inhibitor of Norepinephrine Uptake Devoid of Affinity for Receptors in Rat Brain", *The Journal of Pharmacology and Experimental Therapeutics*, vol. 222, No. 1, 61–65 Mar 26, 1982.

Robertson et al., "Progress in Antidepressant Drugs", *Annual Reports in Medicinal Chemistry*, Chapter 3, pp. 23–32 (1991).

Chouinard et al., "An Early Phase II Clinical Trial of Tomoxetine (LY139603) in the Treatment of Newly Admitted Depressed Patients", *Psychopharmacology*, vol. 83:126–128 (1984).

*Primary Examiner*—Richard L. Raymond
*Attorney, Agent, or Firm*—Joseph A. Jones; Leroy Whitaker

[57]  ABSTRACT

This invention provides N-alkyl-3-phenyl-3-(2-substituted phenoxy)propylamines which are useful to treat neurological disorders associated with norepinephrine imbalance.

18 Claims, No Drawings

N-ALKYL-3-PHENYL-3-(2-SUBSTITUTED PHENOXY) PROPYLAMINES AND PHARMACEUTICAL USE THEREOF

BACKGROUND OF THE INVENTION

In the past few decades, understanding of the biological role of nerve cells (neurons) has greatly increased. Specifically, particular neurons have been implicated in particular diseases. The present invention provides for compounds which inhibit presynaptic biogenic amine uptake in at least one type of neuron, the norepinephrine neuron.

Norepinephrine neurons are found everywhere in the brain, and are also known to exist in other organs of the body, such as the bladder. The compounds of the present invention indirectly stimulate the neurons by inhibiting norepinephrine uptake. Moreover, the adrenal glands are known to secrete norepinephrine in response to stress. Thus, norepinephrine is also called noradrenalin.

Patients with Alzheimer's and Korsakoff's syndrome and depression may have deficiencies of norepinephrine. The present invention is useful in treatment of disorders associated with norepinephrine imbalance. Schildkraut, Neuropharmacology of Affective Disorders, 427 (1973) is an excellent source of background information.

SUMMARY OF THE INVENTION

The present invention provides novel N-alkyl-3-phenyl-3-(2-substituted phenoxy)propylamines which are selective and potent inhibitors of norepinephrine uptake. More specifically, the present invention relates to the compounds of the formula

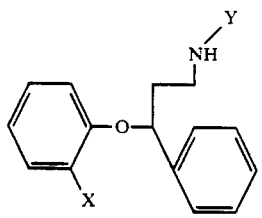

wherein X=I, Br, Cl or $C_1$–$C_4$ alkylthio, and Y=$C_1$–$C_2$ alkyl and the pharmaceutically acceptable acid addition salts thereof.

The invention also provides pharmaceutical formulations comprising a compound of the formula and a pharmaceutically acceptable carrier, diluent or excipient therefor. Further embodiments of the invention are methods for selectively inhibiting the uptake of norepinephrine as well as for treating a variety of disorders which have been linked to decreased neurotransmission of norepinephrine in mammals including substance abuse, depression, narcolepsy, panic disorder, bulimia, and related psychiatric disorders. The compounds of the present invention are useful in treating these mental diseases. In addition, because of the known interaction of the norepinephrine with the urinary system, the compounds are useful to treat urinary incontinence.

DETAILED DESCRIPTION OF THE INVENTION

Preferred compounds are those wherein Y is methyl. The most preferred compound of this series is N-methyl-3-phenyl-3-(2-methylthiophenoxy)propylamine.

The compounds of this invention can exist as the individual stereoisomers as well as the racemic mixture. Accordingly, the compounds of the present invention will include not only the d,l-racemates, but also their respective optically active d- and l-isomers.

As pointed out above, the invention includes the pharmaceutically acceptable acid addition salts of the compounds defined by the above formula. Since the compounds of this invention are amines, they are basic in nature and accordingly react with any number of inorganic and organic acids to form pharmaceutically acceptable acid addition salts. Since the free amines of the invention are typically oils at room temperature, it is preferable to convert the free amines to their corresponding pharmaceutically acceptable acid addition salts, which are routinely solid at room temperature, for ease of handling. Acids commonly employed to form such salts include inorganic acids such as hydrochloric, hydrobromic, hydroiodic, sulfuric and phosphoric acid, as well as organic acids such as paratoluenesulfonic, methanesulfonic, oxalic, parabromophenylsulfonic, carbonic, succinic, citric, benzoic and acetic acid, and related inorganic and organic acids.

Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthathalate, sulfonate, xylenesulfonate, phenylacetate, phenylpropionate, phenylbutyrate, citrate, lactate, β-hydroxybutyrate, glycollate, maleate, tartrate, methanesulfonate, propanesulfonates, naphthalene-1-sulfonate, naphthalene-2-sulfonate, mandelate and the like salts. Preferred pharmaceutically acceptable acid addition salts include those formed with mineral acids such as hydrochloric acid and hydrobromic acid, and especially those formed with organic acids such oxalic acid and maleic acid.

The following compounds further illustrate compounds contemplated within the scope of the present invention: N-ethyl-3-phenyl-3-(2-methylthiophenoxy)propylamine phosphate, N-methyl-3-phenyl-3-(2-t-butylthiophenoxy)propylamine hydrochloride, N-ethyl-3-phenyl-3-(2-iodophenoxy)propylamine formate, N-methyl-3-phenyl-3-(2-ethylthiophenoxy)propylamine succinate, N-methyl-3-phenyl-3-(2-isopropylthiophenoxy)propylamine hydrochloride.

The compounds of this invention in the form of their free bases are high boiling oils, but white crystalline solids in the form of their acid addition salts. The compounds can be prepared in several ways. A particularly useful procedure for preparing compounds represented by the above formula is substantially carried out as described in U.S. Pat. No. 4,018,895, herein incorporated by reference.

EXAMPLE 1

Preparation of
N-methyl-3-phenyl-3-(2-chlorophenoxy)propylamine hydrochloride

A 10.80 g portion of chloroporpiophenone was dissolved in 100 ml of methanol in a 500 ml, 3 necked, round-bottomed flask. The flask was fitted with a nitrogen inlet and a thermometer. The reaction mixture was stirred via magnetic stirring rod, and was held under an atmosphere of nitrogen. While the mixture was cooled in an ice bath, 2.03 g of sodium borohydride was added very slowly. The mixture was removed from the ice bath and then stirred for approximately two hours at room temperature.

The mixture was then evaporated to a yellow oil and diluted with approximately 100 ml of water. The mixture was extracted from the water by washing three times with ether. The ether was then washed two times with water and one time with saturated sodium chloride solution. The resulting mixture was dried over sodium sulfate and evaporated to 11.2 g of yellow intermediate product comprising 3-chloro-1-phenyl-1-propanol.

A 5.07 g portion of the above intermediate was placed into a 3-necked, 250 ml round-bottomed flask which had been flushed with nitrogen. The flask was fitted with a thermometer, a nitrogen inlet and an addition funnel. The compound, 3.31 g of 2-chlorophenol and 7.85 g of triphenylphosphine were magnetically stirred in 70 ml of tetrahydrofuran. A 4.7 ml portion of diethylazodicarboxylate was added dropwise to this mixture. The temperature of the reaction mixture was kept around 25° C. using an ice bath. The addition funnel was rinsed with tetrahydrofuran and the reaction mixture was stirred overnight at approximately room temperature. The mixture was then evaporated to a white solid. Hexane was added to the solid, and the mixture was shaken vigorously. The insoluble triphenylphosphine oxide was then suction-filtered, hexane was again added, and the mixture was shaken and re-filtered. Filtrates were evaporated to 7.89 g of cloudy white oil.

This oil was purified via flash chromatography. The mixture was dry loaded and a solvent system of 100% hexane was used. A 2.50 g portion of the purified compound, 1-(3-chloro-1-phenylpropoxy)-2-chlorobenzene, was then aminated by reacting with methylamine (40% in water), in ethanol at 130° C. for 3 hours. After evaporating the ethanol, water was added. The mixture was extracted two times with ether, and washed two times with water and once with sodium chloride solution. The product was dried over sodium sulfate.

Toluene was added after the evaporation, and evaporated again to produce 830 mg of a cloudy yellow oil. The mixture was extracted two times with ether, and washed two times with water and once with sodium chloride solution. The product was dried over sodium sulfate.

The dried product was submitted to high performance liquid chromatography, by using a solvent system of methylene chloride, methanol and ammonium hydroxide, with the ratio being 100:5:1. A 490 portion of the resulting yellow oil was dissolved by stirring in methanol, and 1.05 equivalents of 12N HCl were added. The methanol was evaporated from the mixture and a yellow oil resulted. The oil was slurried in 20 ml of toluene and 10 ml of heptane and the resulting solid was filtered. A 390 mg portion of off-white solid was thereby obtained. Upon recrystallization, approximately 330 mg of white crystals were obtained. The melting point of the product was 109°-111° C. Analysis: Theory: C, 61.55; H, 6.13; N, 4.49; Found: C, 61.69; H, 6.27; N, 4.49.

EXAMPLE 2

Preparation of
N-methyl-3-phenyl-3-(2-bromophenoxy)propylamine hydrochloride

A 2.65 g portion of the intermediate 3-chloro-1-phenyl-1-propanol as prepared in Example 1 was placed into a 3-necked, 250 ml round-bottomed flask which had been flushed with nitrogen. The flask was fitted with a thermometer, a nitrogen inlet and an addition funnel. The compound, 1.79 g of 2-bromophenol and 4.07 g of triphenylphosphine were magnetically stirred in 40 ml of tetrahydrofuran. A 2.44 ml portion of diethylazodicarboxylate was added dropwise to this mixture. The temperature of the reaction mixture was kept around 25° C. using an ice bath. The addition funnel was then rinsed with tetrahydrofuran and the reaction mixture was stirred overnight at approximately room temperature. The mixture was then evaporated to a yellow-white solid. Hexane was added to the solid and the mixture was shaken vigorously. The insoluble triphenylphosphine oxide was then suction-filtered, hexane was again added, and the mixture was shaken and re-filtered. The filtrates were evaporated to 5.02 g of yellow oil.

This oil was purified via flash chromatography. The mixture was dry loaded and a solvent system of 100% hexane was used. A 2.34 g portion of the resulting yellow oil, 1-(3-chloro-1-phenylpropoxy)-2-bromobenzene, was then aminated by reacting with methylamine (40% in water) in ethanol at 130° C. for 3 hours. After evaporating the ethanol, water was added to the resulting yellow oil. The mixture was extracted with ether, and washed two times with water and once with brine solution. The product was dried over sodium sulfate and evaporated to a yellow oil.

The yellow oil was purified via flash chromotograpy as described in Example 1. The separation resulted in 890 mg of a yellow oil. This oil was dissolved in methanol and 1.05 equivalents of 12N HCl were added. As described in Example 1, an 830 mg portion of off-white crystalline solid was obtained. The melting point of this solid was 109° to 110° C.

Analysis: Theory: C, 53.88; H, 5.37; N, 3.93; Found: C, 54.03; H, 5.47; N, 4.00.

EXAMPLE 3

Preparation of
N-methyl-3-phenyl-3-(2-iodophenoxy)propylamine hydrochloride

A 5.08 g portion of intermediate 3-chloro-1-phenyl propanol as prepared in Example 1 was placed into a 3-necked, 250 ml round-bottomed flask which had been flushed with nitrogen. The flask was fitted with a thermometer, a nitrogen inlet and an addition funnel. The compound, 6.60 g of 2-iodophenol and 7.86 g of triphenylphosphine were magnetically stirred in 70 ml of tetrahydrofuran. A 4.7 ml portion of diethylazodicarboxylate was added dropwise to this mixture. The temperature of the reaction mixture was kept around 25° C. using an ice bath. The addition funnel was rinsed with tetrahydrofuran and the reaction mixture was stirred overnight at approximately room temperature. The mixture was then evaporated to a yellow-white solid. Hexane was added to the solid and the mixture was shaken vigorously. The insoluble triphenylphosphine oxide was then suction-filtered, hexane was again added to the solid, and the mixture was shaken and re-filtered. The filtrates were evaporated to a light yellow oil.

The light yellow oil was purified via flash chromatography. The mixture was dry loaded and a solvent system of 100% hexane was used. A 7.30 g portion of the resulting compound, 1-(3-chloro-1-phenylpropoxy)-2-iodobenzene, was then aminated by reacting with methylamine (40% in water) in ethanol at 130° C. for 3 hours. After evaporating the ethanol, water was added to the resulting yellow oil. The mixture was extracted two times with ether, and washed two times with water and once with brine solution. The product was dried over sodium sulfate.

The amine was then dissolved in methanol and 1.05 equivalents of 12N HCl were added. As described in Example 1, a 1.76 g portion of pale yellow crystals was obtained. The melting point was from 164° to 167° C.

Analysis: Theory: C, 47.58; H, 4.46; N, 3.47; Found: C, 47.70; H, 4.73; N, 3.42.

EXAMPLE 4

Preparation of N-methyl-3-phenyl-3-(2-methylthiophenoxy)propylamine hydrochloride A 4.99 g portion of the intermediate 3-chloro-1-phenyl-1-propanol as prepared in Example 1 was placed into a 3-necked, 250 ml round-bottomed flask which had been flushed with nitrogen. The flask was fitted with a thermometer, a nitrogen inlet and an addition funnel. The compound, 3.52 g of 2-methylthiophenol and 7.69 g of triphenylphosphine were magnetically stirred in 40 ml of tetrahydrofuran. A 4.61 ml portion of diethylazodicarboxylate was added dropwise to this mixture. The temperature of the reaction mixture was kept around 25° C. using an ice bath. The addition funnel was rinsed with tetrahydrofuran and the reaction mixture was stirred overnight at approximately room temperature. During the addition of diethylazodicarboxylate, the mixture became thick, opaque and yellow in color. After approximately one hour, the mixture cleared to a yellow solution. The reaction mixture was evaporated to a yellow solid. Hexane was added to the solid and the mixture was shaken vigorously.

The insoluble triphenylphosphine oxide was then suction-filtered, hexane was again added to the solid, and the mixture was shaken and re-filtered. The filtrates were evaporated to 6.63 g of clear oil. The clear oil was then dissolved in ether. A 2N sodium hydroxide solution was then added. The sodium hydroxide layer was removed and the organic layer was washed once with water and once with saturated sodium chloride solution. The solution was then dried over sodium sulfate. The resulting compound, 1-(3-chloro-1-phenylpropoxy)-2-methylthiobenzene, was then aminated by reacting with methylamine (40% in water) in ethanol at 130° C. for for 3 hours. After evaporating the ethanol, water was added to the resulting yellow oil. The mixture was extracted two times with ether, and washed two times with water and once with brine solution. The product was dried over sodium sulfate.

The product was purified via flash chromatography by wet loading using a methylene chloride, methanol and ammonium hydroxide system with the ratio being 100:5:1. A 870 mg portion of product was recovered.

The amine was dissolved in methanol and 1.05 equivalents 12N HCl were added. Upon recrystallization, as described in Example 1, an 850 mg portion of off-white crystals was obtained.

The melting point of this solid was 143° to 144.5° C.

Analysis: Theory: C, 63.04; H, 6.85;N, 4.32; Found: C, 63.08; H, 6.94;N, 4.23.

As noted above, the compounds of this invention are useful for inhibiting the uptake of norepinephrine. Therefore, another embodiment of the present invention is a method for inhibiting norepinephrine uptake in mammals which comprises administering to a mammal requiring increased neuro-transmission of norepinephrine a pharmaceutically effective amount of a compound of the invention.

The term "pharmaceutically effective amount", as used herein, represents an amount of a compound of the invention which is capable of inhibiting norepinephrine uptake. The particular dose of compound administered will, of course, be determined by the particular circumstances surrounding the case, including the compound administered, the route of administration, the particular condition being treated, and similar considerations. The compounds can be administered by a variety of routes, including the oral, rectal, transdermal, subcutaneous, intravenous, intramuscular or intranasal routes. The oral route of administration is preferred.

The compounds of the invention inhibit the uptake of norepinephrine in mammals in an unexpectedly selective and potent manner. A typical daily dose will contain from about 0.01 mg/kg to about 20 mg/kg of the active compound of this invention. Preferred daily doses will be from about 0.05 mg/kg to 10 mg/kg, ideally from about 0.1 mg/kg to 5 mg/kg.

A variety of physiological functions have been shown to be influenced by norepinephrine levels in the body. As such, the compounds of the present invention are believed to have the ability to treat a variety of disorders in mammals associated with abnormal norepinephrine levels in the body.

The following experiment was conducted to demonstrate the ability of the compounds of the present invention to inhibit the uptake of norepinephrine. This general procedure is set forth by Wong et al., 6 *Drug Development Research* 397 (1985).

Male Sprague-Dawley rats weighing 150–250 g were decapitated and brains were immediately removed. Cerebral cortices were homogenized in 9 volumes of a medium containing 0.32M sucrose and 10 mM glucose. Crude synaptosomal preparations were isolated after differential centrifugation at $1000\times$ g for 10 minutes and $17,000\times$ g for 28 minutes. The final pellets were suspended in the same medium and kept in ice until use within the same day.

Synaptosomal uptake of $^3$H-norepinephrine ($^3$H-NE) was determined as follows. Cortical synaptosomes (equivalent to 1 mg of protein) were incubated at 37° C. for 5 minutes in 1 ml of Krebs-bicarbonate medium containing also 10 mM glucose, 0.1 mM iproniazide, 1 mM ascorbic acid, 0.17 mM EDTA and 50 nM $^3$H-NE. The reaction mixture was immediately diluted with 2 ml of ice-chilled Krebs-bicarbonate buffer and filtered under vacuum with a cell harvester (Brandel, Gaithersburg, Md.). Filters were rinsed twice with approximately 5 ml of ice-chilled 0.9% saline and the uptake of the radiolabeled NE assessed by liquid scintillation counting. Accumulation of $^3$H-NE at 4° C. was considered to be background and was subtracted from all measurements. The concentration of the test compound required to inhibit 50% of the $^3$H-NE accumulation (IC$_{50}$ values) were determined by linear regression analysis.

The results of the evaluation of various compounds of the present invention are set forth below in Table I. As shown in the Table, four compounds are evaluated to determine concentration of the test compound needed to inhibit 50% of norepinephrine, as indicated by IC$_{50}$.

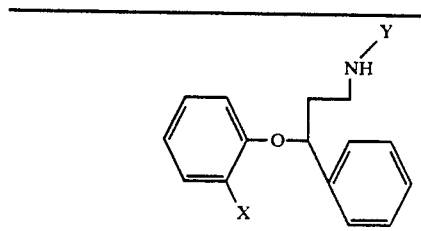

| Compound | | |
|---|---|---|
| X | Y | IC$_{50}$ NE Uptake (nM) |
| I | CH$_3$ | 4.8 |
| Br | CH$_3$ | 4.9 |
| Cl | CH$_3$ | 4.5 |
| CH$_3$S | CH$_3$ | 4.4 |

The compounds of the present invention are preferably formulated prior to administration. Therefore, yet another embodiment of the present invention is a pharmaceutical formulation comprising a compound of the invention and a pharmaceutically acceptable carrier, diluent or excipient therefor.

The present pharmaceutical formulations are prepared by known procedures using well known and readily available ingredients. In making the compositions of the present invention, the active ingredient will usually be mixed with a carrier which may be in the form of a capsule, sachet, paper or other container. When the carrier serves as a diluent, it may be a solid, semisolid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, ointments containing, for example up to 10% by weight of the active compound, soft and hard gelatin capsules, suppositories, sterile injectable solutions and sterile packaged powders.

Some examples of suitable carriers, excipients, and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, methyl cellulose, methyl- and propylhydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide quick, sustained or delayed release of the active ingredient after administration to the patient by employing procedures well known in the art.

The compositions are preferably formulated in a unit dosage form, each dosage containing from about 5 to about 500 mg, more usually from about 25 to about 300 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical carrier.

The following formulation examples are illustrative only and are not intended to limit the scope of the invention in any way.

Formulation 1

Hard gelatin capsules are prepared using the following ingredients:

| | Quantity (mg/capsule) |
|---|---|
| N-methyl-3Ophenyl-3-(2-chlorophenoxy)propylamine | 250 |
| starch, dried | 200 |
| magnesium stearate | 10 |
| Total | 460 mg |

The above ingredients are mixed and filled into hard gelatin capsules in 460 mg quantities.

Formulation 2

A tablet is prepared using the ingredients below:

| | Quantity (mg/capsule) |
|---|---|
| N-methyl-3-phenyl-3-(2-bromophenoxy)propylamine | 250 |
| cellulose, microcrystalline | 400 |
| silicon dioxide, fumed | 10 |
| stearic acid | 5 |
| Total | 665 mg |

The components are blended and compressed to form tablets each weighing 665 mg.

Formulation 3

Tablets each containing 60 mg of active ingredient are made as follows:

| | |
|---|---|
| N-methyl-3-phenyl-3-(2-methylthiophenoxy)propylamine | 60.0 mg |
| starch | 45.0 mg |
| microcrystalline cellulose | 35.0 mg |
| polyvinylpyrrolidone (as 10% solution in water) | 4.0 mg |
| sodium carboxy methyl starch | 4.5 mg |
| magnesium stearate | 0.5 mg |
| talc | 1.0 mg |
| Total | 150.0 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 4

Capsules each containing 80 mg of medicament are made as follows:

| | |
|---|---|
| N-methyl-3-phenyl-3-(2-ethylthiophenoxy)propylamine | 80 mg |
| starch | 59 mg |
| microcrystalline cellulose | 59 mg |
| magnesium stearate | 2 mg |
| Total | 200 mg |

The active ingredient, cellulose, starch and magnesium stearate are blended, passed through a No. 45 mesh U.S. sieve, and filled into hard gelatin capsules in 200 mg quantities.

Formulation 5

Suppositories each containing 225 mg of active ingredient may be made as follows:

| | |
|---|---|
| N-methyl-3-phenyl-1-(2-iodophenoxy)propylamine | 225 mg |
| saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 6

Suspensions each containing 50 mg of medicament per 5 ml dose are made as follows:

| | |
|---|---|
| N-methyl-3-phenyl-3-(2-ethylthiophenoxy)propylamine | 50.00 mg |
| sodium carboxymethyl cellulose | 50.00 mg |
| syrup | 1.25 ml |
| benzoic acid solution | 0.10 ml |
| flavor | q.v. |
| color | q.v. |
| purified water of total | 5.00 ml |

The medicament is passed through a No. 45 mesh U.S. sieve and mixed with the sodium carboxymethyl cellulose and syrup to form a smooth paste. The benzonic acid solution, flavor and color are diluted with some of the water and added, with stirring. Sufficient water is then added to produce the required volume.

Formulation 7

An intravenous formulation may be prepared as follows:

| | |
|---|---|
| N-methyl-3-phenyl-3-(2-chlorophenoxy)propylamine | 100 mg |
| isotonic saline | 1000 ml |

The solution of the above ingredients is administered intravenously at a rate of 1 ml per minute to a subject suffering from depression.

We claim:

1. The compound

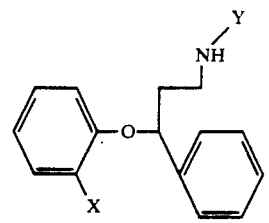

wherein $X = C_1-C_4$ alkylthio and $Y = C_1-C_2$ alkyl and the pharmaceutically acceptable acide addition salts thereof.

2. The compound of claim 1, wherein $X = CH_3S$ and $Y = CH_3$ or a salt thereof.

3. A method for inhibiting norepinephrine uptake in mammals which comprises administering to a mammal requiring altered neurotransmission of norepinephrine an effective amount of a compound or salt of the compound of claim 1.

4. The method of claim 3, wherein the compound is N-methyl-3-phenyl-3-(2-iodophenoxy)propylamine or a salt thereof.

5. A method of treating depression in humans comprising administering to a human suffering from depression an effective anti-depression dose of a compound or salt of the compound of claim 1.

6. The method of claim 5 wherein the compound is N-methyl-3-phenyl-3-(2-iodophenoxy)propylamine or a salt thereof.

7. A method of treating panic disorder in humans comprising administering to a human suffering from panic disorder an effective anti-panic disorder dose of a compound or salt of the compound of claim 1.

8. The method of claim 7, wherein the compound is N-methyl-3-phenyl-3-(2-iodophenoxy)propylamine or a salt thereof.

9. A method of treating narcolepsy in humans comprising administering to a human suffering from narcolepsy an effective anti-narcolepsy dose of a compound or salt of the compound of claim 1.

10. The method of claim 9, wherein the compound is N-methyl-3-phenyl-3-(2-iodophenoxy)propylamine or a salt thereof.

11. A method of treating substance addiction in humans comprising administering to a human suffering from substance addiction an effective anti-substance addiction dose of a compound or salt of the compound of claim 1.

12. The method of claim 11, wherein the compound is N-methyl-3-phenyl-3-(2-iodophenoxy)propylamine or a salt thereof.

13. The method of treating urinary incontinence in humans comprising administering to a human suffering from urinary incontinence an effective anti-urinary incontinence dose of a compound or salt of the compound of claim 1.

14. The method of claim 13, wherein the compound is N-methyl-3-phenyl-3-(2-iodophenoxy)propylamine or a salt thereof.

15. The method of treating bulimia in humans comprising administering to a human suffering from bulimia an effective anti-bulimia dose of a compound or salt of the compound of claim 1.

16. The method of claim 15 wherein the compound is N-methyl-3-phenyl-3-(2-iodophenoxy)propylamine or a salt thereof.

17. A pharmaceutical formulation comprising a compound or salt of claim 1 and one or more acceptable carriers, diluents or excipients therefore.

18. The pharmaceutical formulation of claim 17, wherein the compound is N-methyl-3-phenyl-3-(2-iodophenoxy)propylamine or a salt thereof.

* * * * *

UNITED STATES PATENT AND TRADEMARK OFFICE
CERTIFICATE OF CORRECTION

PATENT NO. : 5,281,624
DATED : January 25, 1994
INVENTOR(S) : Donald R. Gehlert et al It is certified that error appears in the above-indentified patent and that said Letters Patent is hereby corrected as shown below:

Column 10, Line 13, delete "acide", and insert therefor --acid--.

Column 10, Line 24, delete "(2-iodophenoxy)", and insert therefor --(2-methylthiophenoxy)--.

Column 10, Line 32, delete "(2-iodophenoxy)", and insert therefor --(2-methylthiophenoxy)--.

Column 10, Line 39, delete "(2-iodophenoxy)", and insert therefor --(2-methylthiophenoxy)--.

Column 10, Line 46, delete "(2-iodophenoxy)", and insert therefor --(2-methylthiophenoxy)--.

Column 10, Line 54, delete "(2-iodophenoxy)", and insert therefor --(2-methylthiophenoxy)--.

Column 10, Line 63, delete "(2-iodophenoxy)", and insert therefor --(2-methylthiophenoxy)--.

Column 11, Line 3, delete "(2-iodophenoxy)", and insert therefor --(2-methylthiophenoxy)--.

UNITED STATES PATENT AND TRADEMARK OFFICE
CERTIFICATE OF CORRECTION

PATENT NO. : 5,281,624
DATED : January 25, 1994
INVENTOR(S) : Donald R. Gehlert et al It is certified that error appears in the above-indentified patent and that said Letters Patent is hereby corrected as shown below:

Column 12, Line 4, delete "(2-iodophenoxy)", and insert therefor --(2-methylthiophenoxy)--.

Signed and Sealed this

Fifteenth Day of November, 1994

Attest:

BRUCE LEHMAN

Attesting Officer

Commissioner of Patents and Trademarks